United States Patent
Lobdill et al.

(12)
(10) Patent No.: US 6,413,263 B1
(45) Date of Patent: Jul. 2, 2002

(54) STEREOTACTIC PROBE HOLDER AND METHOD OF USE

(75) Inventors: Richard Lobdill, Oceano; Andrew Blatz, San Mateo, both of CA (US)

(73) Assignee: Axon Instruments, Inc., Union City, CA (US)

( * ) Notice: Subject to any disclaimer, the term of this patent is extended or adjusted under 35 U.S.C. 154(b) by 0 days.

(21) Appl. No.: 09/557,873

(22) Filed: Apr. 24, 2000

(51) Int. Cl.[7] .............................................. A61B 19/00
(52) U.S. Cl. ....................................... 606/129; 606/130
(58) Field of Search ................................. 606/130, 129

(56) References Cited

U.S. PATENT DOCUMENTS

| | | | |
|---|---|---|---|
| 3,196,875 A | * | 7/1965 | Pfeiffer ........................ 606/130 |
| 4,465,069 A | * | 8/1984 | Barbier et al. ............... 606/130 |
| 4,998,938 A | | 3/1991 | Ghajar et al. ................ 606/130 |
| 5,618,288 A | | 4/1997 | Calvo ........................... 606/130 |
| 5,643,286 A | | 7/1997 | Warner et al. ............... 606/130 |
| 5,649,936 A | | 7/1997 | Real ............................. 606/130 |
| 5,817,106 A | | 10/1998 | Real ............................. 606/130 |
| 6,283,977 B1 | * | 9/2001 | Ericsson et al. ............. 606/130 |

OTHER PUBLICATIONS

Starr et al. (1998), "Ablative Surgery and Deep Brain Stimulation for Parkinson's Disease," *Neurosurgery* 43(5):989–1015.

Vitek et al. (1998), "Microelectrode–Guided Pallidotomy: Technical Approach and Its Application in Medically Intractable Parkinson's Disease," *J. Neurosurg.* 88:1027–1043.

* cited by examiner

*Primary Examiner*—Cary E. O'Connor
(74) *Attorney, Agent, or Firm*—Dianne E. Reed; Louis L. Wu; Reed & Associates

(57) ABSTRACT

A device and a method are provided for holding a stereotactic probe in position after the probe has been precisely positioned by stereotactic procedures, such as brain surgery. The device, a stereotactic probe holder, is adjustable, as it is capable of being positioned to contact and grip a probe at a position between a stereotactic frame and a patient's head, and is suitable for holding the probe in a desired location. Methods of using the stereotactic probe holder are also provided. The invention is useful in maintaining the proper positioning of probes, such as deep brain stimulators, electrodes, cryoprobes, cannulae, and the like, after the initial placement of the probes during stereotactic surgery.

24 Claims, 2 Drawing Sheets

STEREOTACTIC PROBE HOLDER AND METHOD OF USE

TECHNICAL FIELD

The present invention relates to devices and methods for use in stereotactic surgery, providing devices and methods for holding a probe in place during and after stereotactic surgery. More particularly, the invention provides a device and a method for maintaining the position of a probe, such as an electrode, a deep brain stimulator, a cryoprobe, a cannula, or the like, following stereotactic placement of the probe in a patient's body.

BACKGROUND

Stereotactic techniques enable surgeons and researchers to direct surgical instruments with great accuracy to targets within the central nervous system, particularly the brain, brainstem, and spinal cord of a patient. Stereotactic surgery is typically carried out using a stereotactic frame and associated adapters and devices, which enable the surgeon to guide surgical instruments to identified targets within the brain, spinal cord, or other part of the central nervous system. Stereotactic frames are typically ring-shaped structures mounted to the head of a patient to provide a fixed reference with respect to the patient's brain, and may be used to determine a three-dimensional data set for accurately locating the target site or anatomical structure of interest during a surgical or diagnostic procedure.

A stereotactic frame may comprise two or more parts. For example, the head-mounted frame may fit into another large frame, which may be used to position a probe to be introduced into the patient and to provide support for a drive mechanism used to maneuver a probe to its target position. Typically, a stereotactic frame has a rail, often in the shape of an arc, that extends above and across the patient's skull. A rail-mounted guide can be positioned at any suitable location along the length of the rail to serve as a guide for surgical instruments and drive mechanisms. Commonly used stereotactic frames include the Leksell, the Riechert-Mundinger, the Todd-Wells, and the Brown-Roberts-Wells devices. Examples of stereotactic frames and devices may be found in U.S. Pat. Nos. 5,649,936 and 5,817,106 to Real; U.S. Pat. No. 5,643,286 to Warner et al.; and U.S. Pat. No. 5,618,288 to Calvo. A removable guide mounting to a burr-hole in the skull is disclosed in U.S. Pat. No. 4,998,938 to Ghajar et al.

Stereotactic techniques are used in investigative and experimental surgeries, as well as surgeries performed for diagnostic, prophylactic, or therapeutic purposes. Stereotactic frames are commonly used when performing placement of deep brain stimulators, brain biopsies, tumor removal, and other modalities of deep brain surgery where the surgeon requires guidance to properly position an instrument. In performing these surgeries, a variety of surgical, diagnostic, and observational instruments may be used with stereotactic devices including electrodes, cannulae, catheters, biopsy instruments, stimulators, ablators, heating elements, cryosurgical probes, and the like. Such instruments may be used to affect, alter, or excise tissue, or to place drugs, cells, tissues or devices at a specific location in the brain and central nervous system. Stereotactic surgical techniques are used, for example, in the placement of deep brain stimulators, where ongoing stimulation of specific locations within the brains of patients is used to relieve symptoms of Parkinson's disease and other neurological disorders. Stereotactic techniques are also used for the placement and positioning of catheters, cannulae, and other devices for sampling or for delivery (by microinjection, microdialysis, or other means) of drugs or other therapeutic, diagnostic or experimental agents, cells or tissues, for biopsies, for lesioning, for resection, and the like.

For example, stereotactic techniques using stereotactic frames are useful for microelectrode guidance. Stereotactic microelectrode guidance is used in the treatment of Parkinson's disease, epilepsy, and other neurological conditions, for the placement and positioning of electrodes, such as deep brain stimulators, for localization of brain nuclei and brain mapping, and other probes for neuronal stimulation, neuronal recording, and ablation of precise locations within the brain of a patient.

Any instrument introduced into the brain of a patient may be termed a "probe." Thus, a probe may be a deep brain stimulator, a recording electrode, a cannula, a catheter, an ablator, or other instrument. Probes are typically introduced into the patient's brain through a burr hole in the skull. An important use of stereotactic surgical techniques is for the placement of probes into the brain or other organs, where the probes are intended to remain in place for extended periods of time, or even permanently. The final positioning of a probe in a stereotactic procedure is typically accomplished using a microdrive, which provides greater precision of motion than other, more coarse drive mechanisms.

In order to achieve successful long-term or permanent implantation, the probe is commonly attached securely to a solid structure on the patient, such as the skull, to anchor it in its proper position. Typically, a glue or cement is applied to the portion of the probe adjacent the burr hole, although other methods of securely attaching the probe may also be used, such as sutures, or plates, rings or caps adapted to hold the probe and cover the burr hole. Thus, in order not to lose its precise placement in the brain, brainstem, or spinal cord of the patient, the probe must accurately maintain its position during the anchoring procedure, such as during the setting of the glue or cement. However, attempting to hold the probe at a point at or above the arc of the stereotactic frame allows for movement of the probe within the brain of the patient. In addition, the stereotactic apparatus is typically partially disassembled to expedite the anchoring procedure. Such disassembly can introduce mechanical displacement, disturbing the probe and moving it from its desired location. Incorrect placement of a probe reduces the degree of, or entirely prevents, the success of the surgical procedure. Accordingly, there is a need in the art for devices and methods that maintain the correct position of the probe during anchoring of the probe in the patient and during partial disassembly of the stereotactic apparatus.

SUMMARY OF THE INVENTION

The invention is addressed to the aforementioned need in the art, and provides novel devices and methods for holding a probe, such as a deep brain stimulator, following stereotactic placement of the probe in a desired location in a patient's body, thus providing stability and maintenance of probe placement during potentially disruptive post-placement activities such as removal of a microdrive. The invention provides means to hold a probe in position, following positioning by stereotactic procedures, while means for more permanent immobilization are affixed to the probe for long-term implantation in a patient's brain.

Accordingly, it is an object of the invention to provide a stereotactic probe holder for maintaining a probe in position, where the stereotactic probe holder contacts the probe at a position between a stereotactic frame and a patient's head, and where the stereotactic probe holder comprises an adjustable support, a locking means effective to substantially immobilize the stereotactic probe holder, and a gripping means, attached to the adjustable support, that is effective to hold the probe.

It is another object of the invention to provide a stereotactic probe holder for holding a probe in position, where the stereotactic probe holder contacts the probe at a position between a stereotactic frame and a patient's head, where the adjustable support of the stereotactic probe holder comprises a rotation means capable of rotation around an axis, and a radial positioning means attached to the rotation means that can slide inwardly and outwardly with respect to the rotation means. The stereotactic probe holder further comprises gripping means attached to an end of the radial positioning means, whereby adjustment of the radial positioning means allows movement of the gripping means in a plane substantially orthogonal to the axis of the rotation means.

It is a further object of the invention to provide a method for holding a probe following placement of the probe using a stereotactic apparatus, comprising the steps of providing a stereotactic probe holder that includes a gripper and a locking means, affixing the gripper onto the probe, and applying the locking means to substantially immobilize the stereotactic probe holder so as to maintain the probe in position.

Additional objects, advantages and novel features of the invention will be set forth in part in the description which follows, and in part will become apparent to those skilled in the art upon examination of the following, or may be learned by practice of the invention.

In one aspect, then, the present invention relates to a stereotactic probe holder for maintaining a probe in position following positioning of the probe in a patient's brain, brainstem or spinal cord by stereotactic procedures. The stereotactic probe holder includes a gripper attached to an adjustable support, where the position of the gripper may be adjusted so as to contact a probe at a position between a stereotactic frame and a patient's head. The stereotactic probe holder also includes a locking means capable of substantially immobilizing the stereotactic probe holder so as to hold the probe in position.

In another aspect, the invention relates to the above stereotactic probe holder, wherein the adjustable support comprises a rotation arm capable of rotation around an axis, and a shaft attached to the rotation arm that can slide inwardly and outwardly with respect to the rotation arm. In this aspect, the gripper is attached to the shaft. Adjustment of the rotation arm is effective to maneuver the gripper about the axis. That is, rotating the rotation arm maneuvers the gripper angularly around the axis, while longitudinal adjustment of the rotation arm makes possible displacement of the gripper in a direction parallel to the axis. Adjustment of the shaft is effective to maneuver the gripper in a plane substantially orthogonal to the axis of the rotation arm, by adjusting the length of the radius separating the gripper from the rotation arm.

In another aspect, the invention provides a method for holding a probe following stereotactic probe placement during surgery using stereotactic apparatus, comprising the steps of providing a stereotactic probe holder that includes a gripper and a locking means, affixing the gripper onto the probe in a position between the stereotactic frame and the patient's head, and applying the locking means to substantially immobilize the stereotactic probe holder so as to maintain the probe in position.

BRIEF DESCRIPTION OF THE DRAWINGS

The invention is described in detail below with reference to the following drawings.

DETAILED DESCRIPTION OF THE INVENTION

Figure 1:
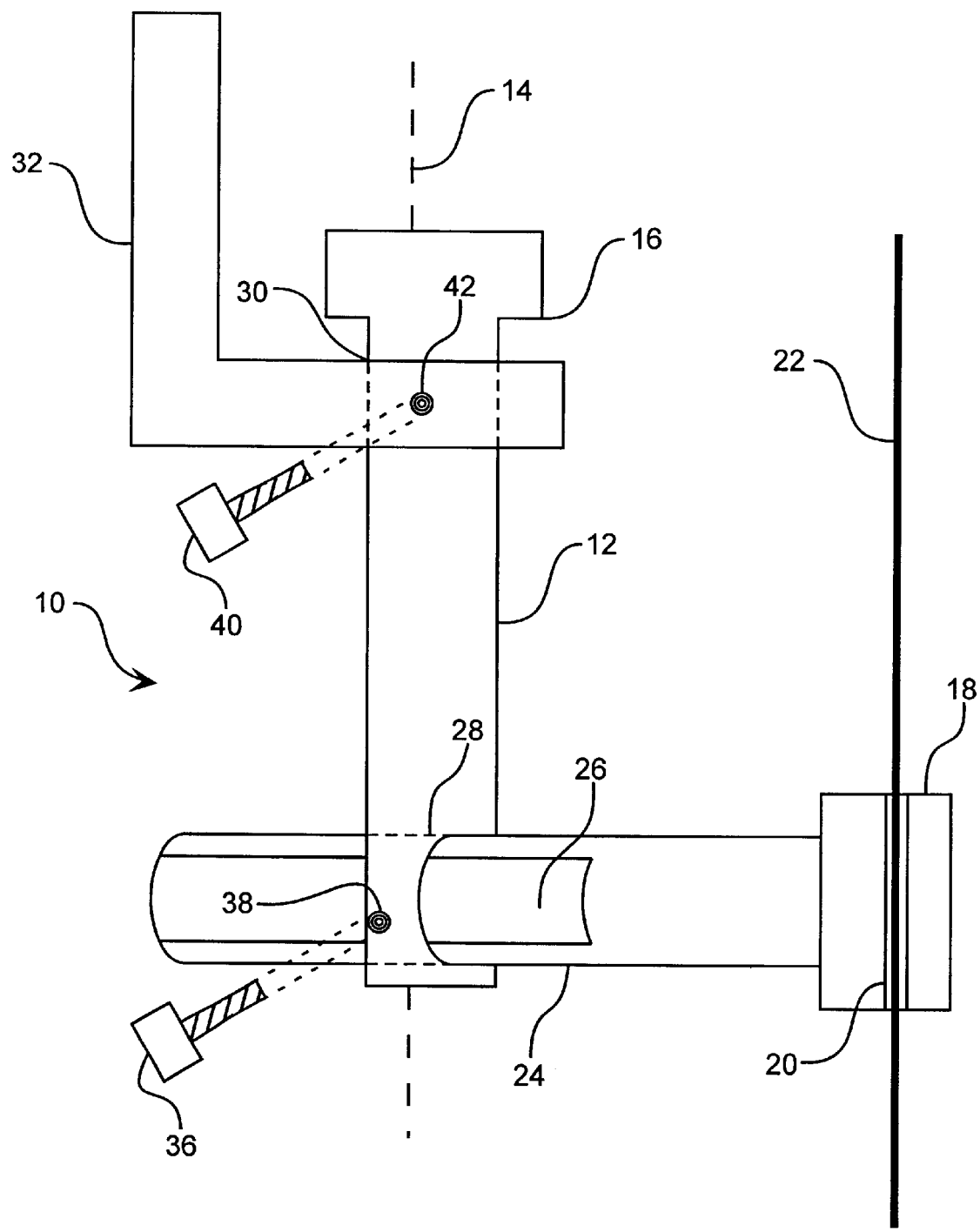
FIG. 1 is a partially cross-sectional partly exploded side-view of a device of the invention, where the gripper is shown attached to a shaft that can slide through an aperture in a cylindrical rotation arm.

Before the present devices and methods are disclosed and described, it is to be understood that unless otherwise indicated this invention is not limited to specific embodiments or to particular surgical procedures, as such may vary. It is also to be understood that the terminology used herein is for the purpose of describing particular embodiments only and is not intended to be limiting.

It must be noted that, as used in the specification and the appended claims, the singular forms "a," "an" and "the" include plural referents unless the context clearly dictates otherwise.

In this specification and in the claims which follow, reference will be made to a number of terms which shall be defined to have the following meanings:

By the term "adjustable" is meant capable of being put into a plurality of positions or orientations. Thus, for example, an "adjustable support" is a support capable of being placed in a plurality of orientations or positions.

By "animal" is meant any animal, including humans.

The term "anchoring means" refers to any means suitable for retaining a probe in proper position for long periods of time following stereotactic surgery, the duration of such periods of time being determined by the purpose of the implantation. Anchoring means include, but are not limited to, plates, sutures, rings, caps, cements, glues, waxes, pastes, silicon derivatives, polymers, and other devices and substances suitable for anchoring a probe in place in a patient's head for an indefinite period of time.

A "drive mechanism" is a device capable of moving a probe, such as a deep brain stimulator, into position. Drive mechanisms, such as microdrives, include but are not limited to manual micropositioners, hydraulic micropositioners, threaded-screw micropositioners, stepper motors, solenoids, and the like.

A "friction fitting" is any means for holding an object by means of friction. Friction fittings include, but are not limited to, receptacles, such as slots, sized to snugly engage objects and to hold them by frictional contact between the objects and the receptacles.

The term "gripper" as used herein refers to a mechanism for restraining or capturing a physical object. Thus, a slot, notch, or groove that is sized to receive and hold an object, as by a friction fit, clamps, spring-plates, magnets, adhesives, or other means for securely and reversibly holding an object are all gripping means.

By "locking means" is meant any means effective to substantially prevent motion of an object to be held in a desired position, and includes setscrews, clamps, magnetic locks, spring-detents, and the like. Setscrews include thumbscrews, which may be tightened readily by hand, and those setscrews that are preferably tightened with the aid of tools or other devices.

The term "patient" as used herein refers to an animal undergoing a stereotactic surgical, diagnostic, or experimental procedure, including a human patient.

The term "probe" as used herein refers to a device to be introduced into the brain of a patient, such as an ablator, a biopsy device, a cannula, a catheter, a cryoprobe, a deep brain stimulator, an electrode, a heating element, a sensor, a surgical instrument, or the like.

By "radial" is meant in a direction substantially parallel to a radius. Thus, a "radial positioning means," such as a "radial positioning arm," is a support capable of holding or placing an object in a plurality of positions along a radius.

By "rotation means" is meant a support capable of rotating about an axis, effective to hold or place an object in any one of a plurality of orientations or positions around an axis. Thus, a "rotation arm" is a support capable of rotating about an axis of rotation.

By "slidable" and "slidably" is meant being capable of motion with respect to an adjacent and contacting object, such as being able to slide along or through an adjacent object.

The term "stereotactic apparatus" refers to equipment useful for precise control of a probe to be inserted into a patient's brain, brainstem or spinal cord. Stereotactic apparati include stereotactic frames that attach to a patient's head, adapters, such as may be used to mount devices to a stereotactic frame, microdrives for precision movement of a probe generally along the longitudinal axis of the probe, translation stages for lateral positioning of a probe, and other devices attached to or used in conjunction with a stereotactic frame.

By the term "stereotactic frame adapter" is meant any device for attaching an instrument to a stereotactic frame, either directly or indirectly. Commonly, stereotactic frame adapters attach to the arcuate portion of a stereotactic frame, and provide for slidable attachment of instruments, although a stereotactic frame adapter may attach to any portion of the stereotactic frame, or to a part attached to the stereotactic frame, and may or may not provide slidable attachment.

The term "stereotactic surgery" as used herein refers to any procedure carried out on a patient, including a human patient, wherein a probe is introduced into the patient using stereotactic techniques and stereotactic apparatus, such as under the guidance or control of a stereotactic frame or other stereotactic device. Stereotactic surgery, as used herein, may be for diagnostic, prophylactic, therapeutic, investigative, experimental, or other purposes.

By "support" is meant any arm, bar, beam, brace, cylinder or other structure capable of supporting or holding an object in a desired position.

In one embodiment, the present invention provides a stereotactic probe holder for maintaining a probe in a position following stereotactic placement of the probe in a desired position.

The invention finds use in surgery performed on patients where a probe, positioned in place by stereotactic techniques, is desired to remain in position after the surgery is completed. In a preferred embodiment, the patient is a human patient. In a particularly preferred embodiment, the probe is applied during brain surgery. In a further preferred embodiment, the probe is an electrode. In a particularly preferred embodiment, the electrode is a deep brain stimulator.

The device of the invention is a stereotactic probe holder comprising a gripper, an adjustable support, and a locking means. The gripper is attached to the adjustable support, where the adjustable support is maneuverable in space effective to bring the gripper into contact with the probe at a position between the stereotactic frame and the patient's head, in order that the gripper can be affixed to the probe. The gripper is adapted to restrain or capture the probe, effective to hold the probe. The locking means is effective to lock the adjustable support into position once the gripper has been affixed to the probe. The device is effective to hold the probe in position when the gripper has been affixed to the probe and the locking means of the apparatus have been engaged.

Any means for holding a probe are suitable for the gripper. For example, the gripper may comprise a slot sized to snugly hold the probe with a friction fit. It will be understood by one of skill in the art that the gripper may comprise adhesives, clamps, clasps, magnets, friction fittings such as slots, or other gripping means to hold the probe. The gripper may further comprise a slide effective to cover a slot after the probe has been inserted therein to enclose a portion of the probe.

The adjustable support may comprise any means effective to permit the maneuvering of the gripper so as to contact and capture the probe at a position between the stereotactic frame and the patient's head, and to provide for locking the adjustable support into place once the gripper has been attached to the probe.

The adjustable support may comprise any support, such as a straight or a curved bar, with the gripper attached to one end of the support. The gripper may be fixably attached to an end of an adjustable support, or may be adjustably attached, as by a ball joint or other adjustable connection capable of being locked into position once proper orientation has been effected.

The adjustable support may also comprise a plurality of supports, operably connected to allow relative motion and mutual support. For example, the adjustable support may comprise two parts, a rotation means and a radial positioning means, with the radial positioning means slidably connected to the rotation means. Preferably, the rotation means comprises a rotation arm that is a bar with an aperture, and the radial positioning means comprises a radial positioning arm that is a shaft, with the gripper attached to an end of the shaft. In such a case, the shaft passes through the aperture of the bar, and is able to slide through the aperture, effective to allow placement of the gripper at a desired radial distance from the bar. In addition, the rotation arm may include a threaded hole for a setscrew, and a setscrew, effective to contact a portion of the shaft within the aperture. Tightening the setscrew against the shaft is effective to lock the shaft into place. Preferably, the shaft has a flat portion, providing a flat surface extending partially along the shaft, whereby tightening of a setscrew against the flat portion of the shaft is effective to immobilize and maintain the shaft in an orientation substantially perpendicular to the direction of motion of the setscrew, thus firmly locating the gripper in the desired position with the proper orientation.

Preferably, the locking means comprises a setscrew, for example a setscrew effective to lock a support in place. In a particularly preferred embodiment, the setscrew is a thumbscrew, allowing for convenient immobilization of the stereotactic probe holder by hand. It will be understood by one of skill in the art that any locking means that is effective to substantially immobilize the adjustable support is suitable for practice of the invention. Suitable locking means may comprise clamps, clips, catches, magnetic locks, pressure plates, setscrews, slides, springs, stops, or other locking means known in the art.

Rotation means may include a bar, or a bar with an aperture. In a preferred embodiment, the rotation means is a bar with an aperture where the bar has an enlarged end, forming a shoulder, effective to prevent the bar from passing completely through a hole sized to accept a portion of the bar. The enlarged end may be rounded, conical, flat, or other shape. In a particularly preferred embodiment, the enlarged end is disk-shaped, and comprises a flat shoulder effective to engage a flat surface adjacent a hole in a frame adapter, effective to allow rotation around an axis of the bar and to orient the bar in a preferred axial orientation with respect to the flat surface when the shoulder portion is in contact with a frame adapter. In an alternative embodiment, the shoulder is rounded, and sized to engage a rounded recess surrounding a hole in the frame adapter, so as to form a ball-joint when the bar is passed through the hole and the rounded shoulder engages the recess. Such a rounded shoulder is effective to prevent the complete passage of the bar through the hole while allowing the bar freedom of movement in a plurality of axial and rotational orientations with respect to the frame adapter.

Referring now to the drawings, in which like numerals indicate like elements throughout, the drawing figures illustrate various views of a stereotactic probe holder 10 of the present invention. As noted above, the adjustable support may comprise one, two or more parts. In a preferred device, the adjustable support comprises a rotation means and a radial positioning means, operably connected to provide adjustable support to the gripper 18 attached to the radial positioning means. In the figures, the rotation means is illustrated as a rotation arm 12 and the radial positioning means is illustrated as a shaft 24, which serves as a radial positioning arm. Thus, as illustrated, the stereotactic probe holder 10 comprises rotation arm 12 and shaft 24 supporting gripper 18 effective to hold the probe 22.

FIG. 1 is a partially cross-sectional, partially exploded side-view of a stereotactic probe holder of the invention. In FIG. 1, the stereotactic probe holder shown generally at 10 comprises rotation arm 12 having an aperture 28 therethrough, shaft 24, and gripper 18 with slot 20. Shaft 24 has a flat portion 26 providing substantially perpendicular contact between shaft 24 and setscrew 36 when the setscrew is tightened. Shaft 24 extends through aperture 28 in rotation arm 12, and is able to slide within the aperture 28 so as to bring gripper 18 closer or farther from the rotation arm 12. Thus, the position of gripper 18 may be adjusted by extension or retraction of shaft 24 with respect to rotation arm 12. Rotation arm 12 extends through hole 30 in the stereotactic frame adapter 32 mounted on stereotactic frame 34. Shoulder 16 of rotation arm 12 is effective to prevent rotation arm 12 from passing completely through hole 30. Rotation arm 12 is able to rotate around its longitudinal axis 14 within hole 30 so as to allow placement of the gripper 18 into a desired position. The turning of setscrew 36, which is screwed into threaded hole 38, is effective to lock shaft 24 into place. The flat end of setscrew 36, which is positioned so as to be able to press against the flat surface 26 of shaft 24, is effective to maintain the proper orientation of shaft 24 and gripper 18. The turning of setscrew 40, which is screwed into threaded hole 42, is effective to lock rotation arm 12 into place when the gripper 18 has been appropriately positioned. Frictional contact between setscrew 40 and rotation arm 12 is effective to hold rotation arm whether or not shoulder 16 is in contact with the stereotactic frame adapter 32 defining hole 30, thus allowing adjustment of rotation arm 12 in a direction generally parallel to the longitudinal axis 14.

It will be understood by those skilled in the art that a number of variations on the aforementioned stereotactic probe holder are possible and suitable for practice of the invention. For example, it will be understood by those skilled in the art that shoulder 16 of rotation arm 12 may be rounded, to provide wide freedom of movement, as well as flat, as illustrated in the figure. Similarly, gripper 18 may comprise a slide or bar suitable for covering slot 20 once probe 22 has been placed in the slot. Gripper 18 may also comprise a magnet effective to hold probe 22, a clamp effective to hold probe 22, or an adhesive surface. In addition, gripper 18 may be adjustably attached to shaft 24 effective to maneuver gripper 18 with respect to shaft 24. Preferably, setscrews 36 and 40 are thumbscrews. However, it will be understood that in other embodiments of the invention one or both setscrews 36 and 40 may be replaced by other locking mechanisms known in the art, such as clamps, clips, springs, bands, and the like.

Figure 2:
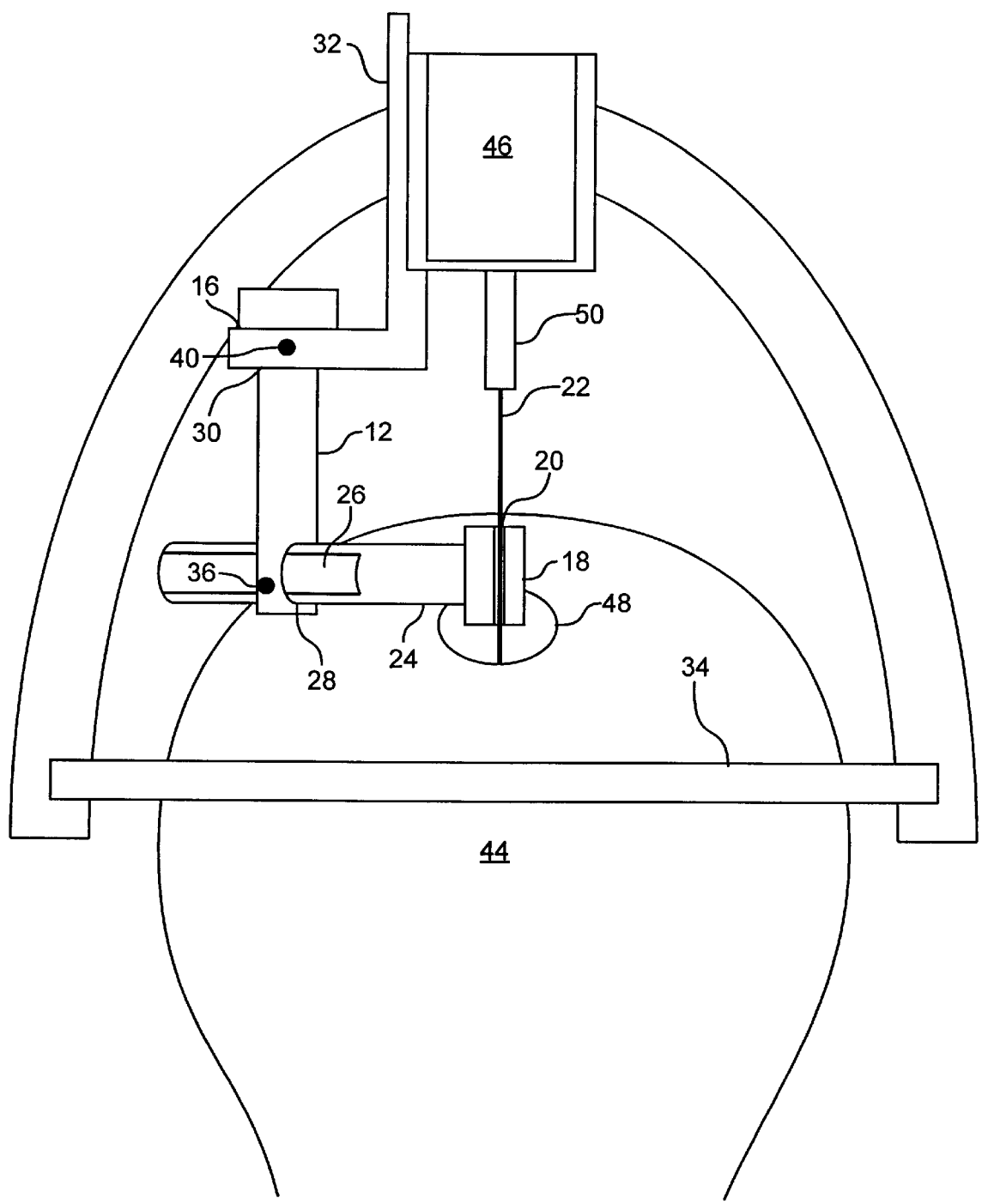
FIG. 2 illustrates the use of the device, shown in place on a stereotactic frame mounted on the head of a patient.

In FIG. 2, a stereotactic probe holder of the invention is shown mounted in place on a stereotactic apparatus to illustrate the spatial relationships of the patient and the device during stereotactic procedures. The device of the invention is identical to that illustrated in FIG. 1, comprising a rotation arm 12, shaft 24, and gripper 18 with slot 20. The head of the patient 44 carries a stereotactic frame 34 on which is mounted microdrive 46 for advancing probe 22 with precision into the brain of the patient; access to the brain is gained via burr hole 48 in the head of the patient 44. The guide cannula 50 is shown in a raised position, providing access to probe 22 by the gripper 18 near to the head of the patient. The stereotactic probe holder is mounted on a stereotactic frame 34, via hole 30 in the frame adapter 32, through which rotation arm 12 is mounted, being prevented from passing completely through the hole 30 by shoulder 16. Rotation arm 12 may be fixed in position by screwing setscrew 40 into threaded hole 42. The shaft 24, which passes through aperture 28 in rotation arm 12, may be fixed in position by screwing setscrew 36 into threaded hole 38.

It will be appreciated by one skilled in the art that the elements of the invention should be made of materials that are sterilizable by common methods, such methods including but not limited to the use of gas, hydrogen peroxide, autoclave, and other means known in the art. Suitable materials include a graphite-reinforced composite or a metal such as aluminum, titanium, and stainless steel, or a high temperature resistant plastic.

In another embodiment, the invention comprises a method for holding a probe in a desired position during a stereotactic procedure using a stereotactic probe holder of the invention. The method comprises the steps of providing a stereotactic probe holder that includes a gripper and a locking means, affixing the gripper onto the probe, and applying the locking means to substantially immobilize the stereotactic probe holder so as to maintain the probe in position. Where the position of the probe must be maintained for a long period of time, the method is useful to hold the probe in the desired position even if other procedures, subsequently performed, might jostle or vibrate the probe, or if parts of the stereotactic apparatus are subsequently removed.

After stereotactic placement of a probe has been performed, the burr hole must be closed and, when the probe is to be left in place, the probe must be immobilized in the correct position. For example, a deep brain stimulator remains in place in a patient's brain indefinitely. Maintenance of proper positioning of the probe is critical to the success of an operation to implant a deep brain stimulator. Surgical cement, plates, rings, rings with caps, sutures, and other methods may be employed to anchor a probe in the proper position in a patient's brain, brainstem or spinal cord. Typically, surgical cement is applied to the burr hole to close the wound and anchor the probe in place by immobilizing an exposed portion of the probe that extends outward from the patient's brain. It will be understood by those of skill in the art that the step of applying anchoring means comprises any means for immobilizing a probe for an indefinite period of time.

For example, the method of the invention may be used to hold a probe in position during application and hardening of surgical cement. In such a case, the steps of the method include providing a stereotactic probe holder that includes a gripper and a locking means, affixing the gripper onto the probe, applying the locking means, and applying anchoring means, where the locking means is effective to substantially immobilize the stereotactic probe holder so as to maintain the probe in position during the application and hardening of the anchoring means. The method of the invention thus holds the probe in place until the surgical cement becomes capable of immobilizing the probe for an indefinite period of time. Suitable cements include methyl methacrylate surgical cement and other cements, waxes, rubbers, pastes, glues, bone substitutes and the like known in the art. In addition, the method of the invention may be used to hold a probe in position during placement of sutures, plates, caps or rings used to immobilize a probe for an indefinite amount of time.

The gripper may be affixed to the probe by gently pressing the gripper onto the probe, whereby the probe is inserted into the slot on the gripper, where the slot is sized to snugly accept and hold the probe by a friction fit. It will be understood by those of skill in the art that other means of affixing the probe are suitable. Thus, the affixing step may comprise the use of any means effective to hold the probe, including use of adhesives effective to grip the probe, clamps effective to clamp the probe, magnets attracted to the probe, slides effective to capture the probe within a slot, and the like. The affixing step may further comprise the step of securing the probe to the gripper. For example, this may be effected by sliding a slide across the slot, enclosing the portion of the probe therein.

The method optionally further comprises the step of removing part of the stereotactic apparatus before applying anchoring means. Such removal of part of the stereotactic apparatus may be useful in order to gain ready access to the burr hole so as to be able to apply anchoring means. For example, removal of a microdrive may provide improved access to the burr hole and so aid in the successful completion of the anchoring procedure and other aspects of the surgery.

The invention finds use in any surgical or experimental procedure utilizing stereotactic techniques and requiring the long-term placement of a probe in a desired location within the body. Application of the present method and use of the novel device disclosed herein provide a means for preventing undesired movement of a probe after stereotactic placement of the probe in a desired position in the patient's central nervous system. For example, in patients undergoing stereotactic surgery for implantation of an electrode, such as a deep brain stimulator, this invention is useful to substantially immobilize an electrode while surgical cement is applied to provide secure permanent attachment of the electrode, thereby improving the surgical outcome. Results obtained from experimental animals undergoing electrode implantation for research purposes will likewise be improved by proper probe placement.

The practice of the present invention will employ, unless otherwise indicated, conventional techniques of patient care, surgical procedures, probe fabrication, and probe placement using stereotactic, imaging, and microrecording techniques, which are within the skill of the art. Such techniques are well explained in the literature. Neurosurgical procedures for stereotactic surgery and probe placement are well known in the art, and are discussed and described in, for example, "Ablative Surgery and Deep Brain Stimulation for Parkinson's Disease" by P. A. Starr, et al., *Neurosurgery* 43:989–1015 (1998) and references cited therein; and "Microelectrode-guided pallidotomy: technical approach and its application in medically intractable Parkinson's disease" by J. L. Vitek, et al., *J. Neurosurgery* 88:1027–1043 (1998) and references cited therein.

It is to be understood that while the invention has been described in conjunction with preferred specific embodiments thereof, the foregoing description, as well as the example to follow, are intended to illustrate and not to limit the scope of the invention. Other aspects, advantages and modifications within the scope of the invention will be apparent to those skilled in the arts to which the invention pertains.

All patents and publications mentioned herein, both supra and infra, are hereby incorporated by reference in their entirety.

EXAMPLE

This example illustrates use of an apparatus of the invention. In this example, a deep brain stimulation electrode is placed in a sensorimotor globus pallidus interna (Gpi) brain nucleus of a patient for treatment of symptoms of Parkinson's disease. A Leksell Stereotactic Coordinate Frame (Elekta Instruments, Stockholm, Sweden), recording apparatus (Guideline System 3000, Axon Instruments, Inc., Foster City, Calif.), and microdrive (Axon Clinical Micropositioner, Axon Instruments) are used in this procedure. A stereotactic probe holder of the invention is attached to an adapter attached to the stereotactic frame.

The patient in need of deep brain stimulation is prepared for surgery and the stereotactic frame is mounted to the patient's head with adjustable posts and fixation screws according to standard procedures. The stereotactic frame provides the basis for target coordinate determination and holds the patient still during treatment. The initial target coordinates are selected based on the mid-commissural point of the anterior commissure-posterior commissure line. Target co-ordinates for the sensorimotor Gpi based on the parasagittal plane are lateral 20, anterior 3, and ventral 5 (from the atlas *Introduction to Stereotaxis with an Atlas of the Human Brain,* by Schaltenbrand, G. and Bailey, P., Stuttgart, Thieme, 1959). After application of local anesthetic, a 2-inch incision of the scalp is made and the cranium is opened by drilling a small burr hole in the skull. The patient is placed in a supine position during this procedure in order to reduce the likelihood of an air embolism. Following the opening of the cranium, the patient's head is elevated to about 30° and remains in that position for the rest of the procedure.

Electrode placement is performed by standard procedures. In these procedures, the deep brain stimulating electrode is placed within a guide cannula, and both electrode and guide cannula are inserted into the brain of the patient under stereotactic guidance. Only the deep brain stimulating electrode is driven the full distance into the brain, the guide cannula entering the brain only part of the way to the target site. The microdrive is used to advance the deep brain stimulating electrode into the patient's brain. Stereotactic target localization is aided and confirmed by microelectrode recording. After the deep brain stimulating electrode is located in the desired position, the deep brain stimulator is clamped above the microdrive (above being distal to the head of the patient), and the guide cannula is raised, exposing a portion of the deep brain stimulating electrode near to the skull of the patient.

The stereotactic probe holder of the invention is then used to immobilize the deep brain stimulating electrode, near to the skull, thereby preventing movement of the probe during subsequent procedures. Reference to FIG. 2 illustrates the configuration of the apparatus of this example. In this example, the setscrews are thumbscrews, able to be tightened and loosened by hand. With the setscrews loosened, thereby allowing adjustment of the radial positioning arm and of the rotation arm, the gripper is placed alongside the deep brain stimulating electrode at a position between the stereotactic frame and the patient's head. The gripper is affixed to the deep brain stimulating electrode, so that the deep brain stimulating electrode is fitted snugly into the slot of the gripper, providing a firm grip on the deep brain stimulating electrode. The setscrews are tightened by hand after the gripper has been affixed to the probe, preventing movement of the rotation arm and radial positioning arm which support the gripper, immobilizing the stereotactic probe holder, thereby immobilizing the deep brain stimulator. The microdrive is then removed to allow for access to the burr hole. Excess blood and tissue are gently removed from the area to prepare for closure of the surgical opening. Surgical cement (methyl methacrylate, Aldrich Chemical Company, Milwaukee, Wis.) is applied to the burr hole and an exposed portion of the deep brain stimulating electrode to provide a substantially permanent mechanically stable support for the implanted electrode. After the cement has become firm, and is able to immobilize the deep brain stimulating electrode by itself, the deep brain stimulating electrode is released from the gripper, and the stereotactic probe holder and the remaining stereotactic apparatus are removed. The neurosurgery is then completed with appropriate final procedures. The patient is then sedated for surgical placement of the chest lead and controller which drive the implanted deep brain stimulator, following which the patient is provided postoperative care.

What is claimed is:

1. A stereotactic probe holder for maintaining a probe in position adjacent to a stereotactic apparatus mounted on the head of a patient, comprising:
   a gripper effective to hold the probe;
   a shaft operably attached to the gripper and comprising a flat portion;
   an adjustable support operably attached to the gripper and effective to place the gripper in a position between the stereotactic frame and the patient's head; and
   a locking means effective to substantially immobilize the adjustable support, thereby holding the probe in position, wherein the locking means, when tightened, engages the flat portion of the shaft in frictional contact effective to clamp the shaft to the support such that the gripper is maintained in position and in proper orientation.

2. The stereotactic probe holder of claim 1, wherein the probe comprises a deep brain stimulator.

3. A stereotactic probe holder for maintaining a probe in position adjacent to a stereotactic apparatus mounted on the head of a patient, the stereotactic apparatus comprising a stereotactic frame and a stereotactic frame adapter, comprising:
   a gripper effective to hold the probe;
   an adjustable support operably attached to the gripper and effective to place the gripper in a position between the stereotactic frame and the patient's head, wherein the adjustable support comprises a rotation means with an axis of rotation, and a radial positioning means attached to the gripper and attached to the rotation means in a manner effective to allow movement of the positioning means, wherein the radial positioning means has a flat portion; and
   a locking means effective to substantially immobilize the adjustable support, thereby holding the probe in position, wherein the locking means, when tightened, engages the flat portion of the radial positioning means in frictional contact effective to clamp the shaft to the support such that the gripper is maintained in position and in proper orientation.

4. The stereotactic probe holder of claim 3, wherein the stereotactic frame adapter comprises a hole therethrough.

5. The stereotactic probe holder of claim 4, wherein the rotation means comprises a substantially cylindrical bar.

6. The stereotactic probe holder of claim 5, wherein the bar extends through the hole.

7. The stereotactic probe holder of claim 6, wherein the bar is capable of rotation around the axis of rotation within the hole.

8. The stereotactic probe holder of claim 4, wherein the rotation means comprises a substantially cylindrical bar with an aperture.

9. The stereotactic probe holder of claim 8, wherein the radial positioning means extends through the aperture.

10. The stereotactic probe holder of claim 9, wherein the radial positioning means is capable of sliding through the aperture, thereby allowing positioning of the gripper at a desired distance from the rotation means.

11. The stereotactic probe holder of claim 3, wherein the gripper is selected from the group consisting of adhesives, clamps, clasps, magnets, and friction fittings.

12. The stereotactic probe holder of claim 11, wherein the friction fitting comprises a slot sized to accept the probe.

13. The stereotactic probe holder of claim 3, wherein the locking means comprises a setscrew and a corresponding threaded recess.

14. The stereotactic probe holder of claim 3, wherein the rotation means comprises a substantially cylindrical object with a first radius and an end portion comprising a second radius larger than the first radius.

15. The stereotactic probe holder of claim 3, wherein the probe comprises a deep brain stimulator.

16. A stereotactic probe holder for maintaining a probe in position adjacent to a stereotactic apparatus including a stereotactic frame adapter with a hole there through, a threaded bore communicating with the hole, and a first setscrew threadably contained within the threaded bore, the apparatus mounted on the head of a patient, comprising:
   a gripper with a slot;
   a shaft operably attached to the gripper and comprising a flat portion;
   a rotation arm with an axis of rotation, an aperture sized to accept the shaft, and a threaded recess communicating with the aperture; and
   a second setscrew threadably contained within the threaded recess in the rotation arm, wherein the slot is sized for holding the probe, wherein the shaft extends into the aperture, the second setscrew is effective to clamp the shaft in the aperture by providing frictional contact between the flat portion of the shaft and the second setscrew such that the gripper is maintained in position and in proper orientation when the second setscrew is tightened, and the rotation arm extends through the hole and is capable of motion therein, whereby tightening the first setscrew is effective to prevent such motion.

17. The stereotactic probe holder of claim 16, wherein the motion of the rotation arm comprises rotation around the axis of rotation.

18. A method for holding a probe following stereotactic positioning of the probe in a patient's head using a stereotactic apparatus including a stereotactic frame, comprising the steps of:

providing a stereotactic probe holder with a gripper and locking means;

affixing the gripper onto the probe in a position between the stereotactic frame and the patient's head;

locking the stereotactic probe holder into position by applying the locking means, whereby the affixing step is effective to hold the probe to the gripper and the locking step is effective to substantially immobilize the stereotactic probe holder and thereby to maintain the probe in position; and removing part of the stereotactic apparatus while the probe is substantially immobilized.

19. The method of claim 18, wherein the locking step is effected by means of a setscrew.

20. The method of claim 19, wherein the setscrew is a thumbscrew.

21. The method of claim 18, further comprising the step of applying an anchoring means to the probe, wherein the anchoring means is effective to substantially immobilize the probe.

22. The method of claim 21, wherein the anchoring means is selected from the group consisting of plates, sutures, rings, caps, cements, glues, waxes, pastes, silicone derivatives, polymers, and combinations thereof.

23. The method of claim 18, wherein the method of affixing the gripper onto the probe is selected from the group consisting of contacting the probe with an adhesive adherent to the gripper, clamping the probe to the gripper, constraining the probe with a clasp attached to the gripper, attracting the probe to the gripper with a magnet adherent to the gripper, and holding the probe by a friction fitting.

24. The method of claim 23, wherein the friction fitting is a slot sized to accept the probe.

\* \* \* \* \*